United States Patent [19]

Gadras et al.

[11] Patent Number: 5,180,827

[45] Date of Patent: Jan. 19, 1993

[54] 2-(3-PYRIDYL) PROPANENITRILE DERIVATIVES

[75] Inventors: Alain Gadras, Lyons; Regis Pepin, Rilleux La Pape, both of France

[73] Assignee: Rhone-Poulenc Agrochimie, Lyons, France

[21] Appl. No.: 636,106

[22] Filed: Dec. 31, 1990

Related U.S. Application Data

[62] Division of Ser. No. 326,004, Mar. 20, 1989, Pat. No. 4,999,357.

[30] Foreign Application Priority Data

Mar. 29, 1988 [FR] France ............................ 88 04411

[51] Int. Cl.$^5$ ...................... C07F 7/02; C07D 213/57; C07D 213/78
[52] U.S. Cl. ..................... 546/14; 546/300; 546/329; 546/330
[58] Field of Search ................ 546/329, 330, 300, 14

[56] References Cited

U.S. PATENT DOCUMENTS

| | | | |
|---|---|---|---|
| 4,639,447 | 1/1987 | Roeser et al. | 514/222 |
| 4,743,603 | 5/1988 | Bulot | 514/235.5 |
| 4,999,357 | 3/1991 | Gadras et al. | 514/277 |

Primary Examiner—Alan L. Rotman

Attorney, Agent, or Firm—Burns, Doane, Swecker & Mathis

[57] ABSTRACT

The invention relates to the 2-(3-pyridyl)-propanenitrile intermediates of formula (V):

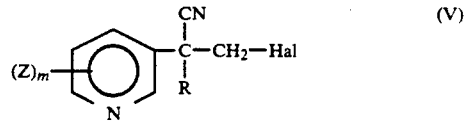

in which:
R denotes
 a lower alkyl radical, optionally substituted with one or more substituents chosen from halogen, and preferably chlorine, fluorine or bromine, atoms, a lower alkoxy radical and a radical —$(CH_2)_x Si\ R_1R_2R_3$, $x=0$ or 1 and $R_1$, $R_2$ and $R_3$, which may be identical or different, being lower alkyl, lower alkoxy, aryl (in particular phenyl) or aralkyl (in particular benzyl);
 an alkenyl, and preferably allyl, radical, optionally substituted as when R denotes alkyl or with a $C_1$ to $C_3$ alkyl group;
Hal denotes a halogen atom;
Z denotes a lower alkyl or lower alkoxy radical; and
m denotes 0, 1 or 2, the groups Z being identical or different when m is 2.

10 Claims, No Drawings

2-(3-PYRIDYL) PROPANENITRILE DERIVATIVES

This application is a divisional of application Ser. No. 07/326,004, filed Mar. 20, 1989 now U.S. Pat. No. 4,999,357.

The present invention relates to new compounds, for use as plant-protection agents, containing 3-pyridyl-β-phenoxy or -(phenylthio)nitrile groups. It also relates to the processes for preparing the said compounds and to the products which are useable, where appropriate, by way of intermediates in the preparation processes. Next, it relates to the use of these compounds by way of fungicides, to the fungicidal compositions based on these compounds and to the processes for controlling fungal diseases of crops using these compounds. It also relates to a product of multiplication of cultivated plants, which has undergone a protective treatment with a compound of the invention.

Many products containing pyridyl groups, in particular fungicides, are already known. In particular, from Patent Application EP-A-145,260, fungicides derived from 2-(3-pyridyl)-2-(phenylamino)acetic acid are known. From Patent Application EP-A-214,793, fungicides derived from 2-aryl-3-pyridylpropionitriles are known.

An object of the present invention is to propose other broad-spectrum fungicidal compounds which are useful, in particular, in the treatment of diseases of the stem base such as eyespot, or of the leaf such as mildew, septoriosis, pyriculariosis, fusarioses or rhynchosporiosis, and diseases caused by pathogenic fungi such as Botrytis, Phoma, Aschochyta and Alternaria in crops as diverse as cereals, vine, rice, maize and soya, for example.

The invention hence relates, in the first place, to the compounds of formula (I) shown at the end of the description in which:

A denotes a linear alkylene chain containing at most six carbon atoms, for example dimethylene or methylene, or a branched alkylene chain containing at most six carbon atoms, with the proviso that the linear chain is other than methylene, for example ethylethylene.

R denotes:
- a lower alkyl radical, optionally substituted (in particular with one or more substituents chosen from halogen atoms, lower alkoxy and lower alkylthio radicals and a radical —$(CH_2)_x SiR_1R_2R_3$, $x=0$ or $1$ and $R_1$, $R_2$ and $R_3$, which may be identical or different, being lower alkyl, lower alkoxy, aryl (in particular phenyl), or aralkyl (in particular benzyl));
- a 3- to 7-membered cycloalkyl radical (in particular cyclopropyl, cyclobutyl, cyclopentyl or cyclohexyl), which is itself optionally substituted in the same manner as the alkyl radical;
- an aralkyl radical (in particular benzyl or phenethyl), optionally substituted in the same manner as the alkyl radical;
- a mono- or polyunsaturated lower alkenyl or alkynyl radical, optionally substituted in the same manner as the alkyl group, with the proviso that there is no unsaturation at the alpha-position with respect to the carbon bearing the CN group; in addition, R is H if A is other than methylene.

$X = O$ or $S$.

Y denotes a halogen (in particular fluorine, chlorine or bromine) atom, a lower alkyl radical, a lower haloalkyl (in particular fluoroalkyl) radical, a lower alkoxy radical, a lower haloalkoxy (in particular fluoroalkoxy) radical, a lower alkylthio radical, a lower haloalkylthio (in particular fluoroalkylthio) radical, a lower alkoxycarbonyl radical, a lower haloalkoxycarbonyl (in particular lower fluoroalkoxycarbonyl radical), a lower alkanoyloxy radical, a lower haloalkanoyloxy (in particular fluoroalkanoyloxy) radical, an aryl (in particular phenyl) radical, an aralkyl (in particular benzyl) radical, a cycloalkyl radical containing 3 to 7 carbon atoms, or a cyano or nitro or hydroxyl radical.

$n =$ positive integer less than 6 or zero, it being possible for the groups Y to be identical or different when n is larger than 1.

Z denotes a lower alkyl or lower alkoxy radical (preferably methyl, ethyl or methoxy).

$m = 0$, 1 or 2, the groups Z being identical or different when $m = 2$.

Within the meaning of the present text, the adjective lower, when it qualifies an organic radical, means that this radical contains at most six carbon atoms. This radical can be linear or branched.

The compounds of formula (I) can form various addition salts with suitable acids, which can be inorganic acids such as, e.g., hydrochloric acid sulphuric acid or phosphoric acid, or organic acids such as, e.g., succinic acid, fumaric acid, maleic acid, oxalic acid or tartaric acid. These various salts are included within the scope of the present invention, most especially when they are acceptable in agriculture (i.e., acceptable for the treated plants).

They may be prepared according to methods which are known per se, for example by dissolving the compound (I) in a suitable solvent, followed by reaction with a suitable acid.

The compounds according to the formula (I) all contain an asymmetrically substituted carbon atom situated at the alpha-position with respect to the pyridyl group. As a result, each of the compounds according to the formula (I) can exist in several stereoisomeric forms, the levels of antifungal activity of which can differ from one another. These stereoisomeric forms, as well as the optically active or racemic mixtures thereof, are also included within the scope of the present invention.

Among the compounds of formula (I) described above, the following variants, taken alone or in combination, will be preferred:

R denotes
- a lower alkyl radical, optionally substituted with one or more substituents chosen from halogen, and preferably chlorine and fluorine, atoms, a lower alkoxy radical and a radical —$(CH_2)_x Si\ R_1R_2R_3$, $x = 0$ or $1$ and $R_1$, $R_2$ and $R_3$, which may be identical or different, being lower alkyl, lower alkoxy, aryl (in particular phenyl) or aralkyl (in particular benzyl);
- an alkenyl, and preferably allyl, radical, optionally substituted as when R denotes alkyl or with a $C_1$ to $C_4$ alkyl group;

A denotes a linear alkylene radical containing at most 4 carbon atoms, and preferably methylene or dimethylene or propylene;

$X = 0$;

$n = 1$, 2 or 3;

Y = lower haloalkoxy, preferably containing 1 to 3 carbon atoms, advantageously trifluoromethoxy, lower haloalkyl, preferably containing 1 to 3 carbon atoms, advantageously trifluoromethyl, or halogen (preferably chlorine or bromine);

m=0.

Furthermore, it was found to be especially advantageous, in the context of the abovementioned applications, to use the compounds of formula (II) in which:

R, n and Y have the same meaning as in the formula (I), and preferably

R denotes a lower alkyl radical, optionally substituted with one or more substituents chosen from halogen, and preferably chlorine, fluorine or bromine, atoms, a lower alkoxy radical and a radical —$(CH_2)_x$-$SiR_1R_2R_3$, x=0 or 1 and $R_1$, $R_2$ and $R_3$, which may be identical or different, being lower alkyl, lower alkoxy, aryl (in particular phenyl) or aralkyl (in particular benzyl);

an alkenyl, and preferably allyl, radical, optionally substituted as when R denotes alkyl or with a $C_1$ to $C_3$ alkyl group;

Y=lower haloalkoxy, preferably containing 1 to 3 carbon atoms, advantageously trifluoromethoxy, lower haloalkyl, preferably containing 1 to 3 carbon atoms, advantageously trifluoromethyl, or halogen (preferably chlorine or bromine);

n=1, 2 or 3, it being possible for Y to be identical or different when n=2 or 3.

Taking into account the possibilities proposed above, taken separately or in combination, it was found to be preferable, by reason of the fungicidal properties, to use the compounds of formula (I) or (II) in which:

Y is a halogen, and preferably bromine or chlorine, atom.

Taking into account the possibilities proposed above, taken separately or in combination, it was found to be preferable, by reason of the fungicidal properties, to use the compounds of formula (I) or (II) in which n=1 or 2.

Taking into account the possibilities proposed above, taken separately or in combination, it was found to be preferable., by reason of the fungicidal properties, to use the compounds of formula (I) and/or (II) in which Y is at the 3- and/or 4-position(s).

Taking into account the possibilities proposed above, taken separately or in combination, it was found to be preferable, by reason of the fungicidal properties to use the compounds of formula (I) or (II) in which R is a $C_1$-$C_6$ alkyl radical.

The subject of the invention is also a process for preparing the products according to the invention.

In the case where A is a methylene chain, a process consists in reacting, in a first stage, a compound of formula (III), in which Z, R and m have the same meaning as in the formula (I) with a dihalomethylene of the formula (IV), Hal denoting a halogen, and preferably chlorine or bromine, atom, in a basic medium in a mole ratio III/II preferably of between 0.8 and 1.2, optionally in the presence of an inert solvent, leading to the compound of formula (V).

As a guide, inorganic bases such as, e.g., sodium hydroxide or potassium hydroxide and alkali metal or alkaline earth metal carbonates, and organic bases such as alkali metal alcoholates, e.g. sodium ethanolate, may be mentioned. From 0.5 to 3 molar equivalents of base will preferably be used.

As a solvent, polar aprotic solvents such as, e.g. dibutyl ether, diisopropyl ether, THF, diisoamyl ether or the dihalomethylene of formula (IV) itself may be mentioned. If desired, this reaction can be performed in the presence of a suitable catalyst. As a useable catalyst, phase transfer catalysts such as, e.g., quaternary ammonium derivatives, e.g. tetrabutylammonium chloride or methyltri($C_8$-$C_{10}$ alkyl)ammonium chloride, may be mentioned.

The temperature is preferably between 20° C. and 100° C. or the refluxing temperature of the solvent when there is one.

Then, in a second stage, the process consists in reacting the compound of formula (V) with the compound of formula (VI) in which X, Y and n have the same meaning as in formula (I), in the presence of a strong base such as alkali metal hydrides or alkali metal alcoholates, optionally in the presence of a suitable polar aprotic solvent such as, e.g., dimethylformamide, dimethylacetamide, dimethyl sulphoxide, acetonitrile or N-methylpyrrolidone, mentioned in the first stage, in a mole ratio (V)/(VI) preferably of between 0.8 and 1.2, and at a temperature preferably of between 20° C. and 100° C. or the refluxing temperature of the solvent when there is one.

The compounds of formulae (IV) and (VI) are prepared in a known manner. The compounds (III) may be prepared according to the following method:

A compound of formula (IX) in which m and Z have the same meaning as in the formula (I) is reacted with a compound of formula RHal, R having the same meaning as in the formula (I) and Hal denoting a halogen atom, in a mole ratio preferably of between 0.8 and 1.2, in the presence of a strong organic or inorganic base and optionally of a suitable polar aprotic solvent such as, e.g. dimethylformamide, dimethylacetamide, dimethyl sulphoxide, acetonitrile or N-methylpyrrolidone, at a temperature advantageously of between 20° C. and 100° C., or the refluxing temperature of the solvent if there is one.

As a strong base, alkali metal hydrides, alkali metal alcoholates, sodium hydroxide or potassium hydroxide may be mentioned.

If desired, this reaction can be performed in the presence of a suitable catalyst. As a useable catalyst, phase transfer catalysts such as, e.g., quaternary ammonium derivatives, e.g. tetrabutylammonium chloride or methyltri($C_8$-$C_{10}$ alkyl)ammonium chloride, may be mentioned.

In the case where A is other than methylene, a process consists, in a first stage, in reacting the compound of formula (IX) with a compound of formula (VII) in which A is other than methylene and Hal corresponds to a halogen atom, in the presence of a strong base, in a mole ratio (VII)/(IX) preferably of between 0.8 and 1.2, optionally in the presence of a polar aprotic solvent, leading to the compound of formula (VIII); then, in a second stage, in reacting the compound of formula (VIII) with a compound of formula Hal-R, Hal being a halogen atom and R having the same meaning as in the formula (I) except for H, in a basic medium in a mole ratio preferably of between 0.8 and 1.2, optionally in the presence of a polar aprotic solvent as mentioned in stage 2, and at a temperature of between 20° C. and 100° C., or the refluxing temperature of the solvent if there is one.

At the end of the reaction, irrespective of the process used, the compound formed is isolated from the reaction medium by the usual means such as, e.g., distillation of the solvent or by crystallization of the product in the reaction medium or by filtration, and then, if necessary, it is then purified, for example by recrystallization in a suitable solvent or by chromatography.

The subject of the invention is also the compounds which are useable, where appropriate, by way of intermediates in the preparation processes described above, and of formulae V and VIII, in which Z R, Y, X, n and m have any one of the meanings stated in the description hereinbefore.

The present invention also relates to the use of the compounds of formula I by way of fungicides.

The compounds according to the invention may be used for both the preventive and the curative control of fungi, in particular of the basidiomycetes, ascomycetes, adelomycetes or fungi imperfecti type, especially rusts, mildew, eyespot, fusariosis, helminthosporiosis, septorioses and rhizoctonia diseases of vegetables and plants in general, and especially of cereals such as wheat, barley, rye, oats and hybrids thereof, and also rice and maize. The compounds according to the invention are especially active against fungi, in particular of the basidiomycetes, ascomycetes, adelomycetes or fungi imperfecti type, such as *Botrytis cinerea, Erysiphe graminis, Puccinia recondita, Piricularia oryzae, Cercospora beticola, Puccinia striiformis, Erysiphe cichoracearum, Fusarium oxysporum (melonis), Pyrenophora avenae, Septoria tritici, Venturia inaequalis, Whetzelinia sclerotiorum, Monilia laxa, Mycosphaerella fijiensis, Marssonina panettoniana, Alternaria solani, Aspergillus niger, Cercospora arachidicola, Cladosporium herbarum, Helminthosporium oryzae, Penicillium expansum, Pestalozzia sp, Phialophora cinerescens, Phoma betae, Phoma foveata, Phoma lingam, Ustilago maydis, Verticillium dahliae, Ascochyta pisi, Guignardia bidwellii, Corticium rolfsii, Phomopsis viticola, Sclerotinia sclerotiorum, Sclerotinia minor, Coryneum cardinale, Rhizoctonia solani, Uncinula necator, Podosphaera leucotricha* and *Fusicladium sp.*

They are also active as well against the following fungi: *Acrostalagmus koningi,* Alternaria sp., Colletotrichum sp., *Corticium rolfsii, Diplodia natalensis, Gaeumannomyces graminis, Gibberella fujikuroi, Hormodendron cladosporioides, Lentinus degener* or *tigrinus, Lenzites quercina, Memnoniella echinata, Myrothecium verrucaria, Paecylomyces varioti, Pellicularia sasakii, Phellinus megaloporus, Polystictus sanguineus, Poria vaporaria, Sclerotium rolfsii, Stachybotris atra, les Stereum,* Stilbum sp., *Trametes trabea, Trichoderma pseudokoningi* and *Trichothecium roseum.*

The compounds of the invention are especially advantageous on account of their broad spectrum in respect of diseases of cereals, (mildew, rust, eyespot, helminthosporioses, septorioses and fusarioses). They are also of great interest by reason of their activity against grey mold (Botrytis) and piricularioses and, as a result, they may be applied on crops as varied as vine, market garden crops and cultivated trees, and tropical crops such as groundnut, banana, coffee, pecan nut, rice and the like.

In view of their absence of phytoxicity, the compounds may be used for the protection of the products of multiplication of plants against diseases caused by fungi.

The invention hence relates, in addition, to a product of multiplication of cultivated plants which has undergone a protective treatment with a compound of the invention.

The term "product of multiplication" denotes all the generative parts of the plant which can be used for the multiplication of the latter. There will be mentioned, e.g., the grains (seeds in the narrow sense), roots, fruit, tubers, bulbs, rhizomes, stem parts, seedlings (shoots) and other parts of plants. There will also be mentioned germinated plants and young seedlings which have to be transplanted after germination or after emergence from the soil. These young seedlings can be protected before transplantation by a total or partial treatment by immersion.

Thus, these compounds may be used in the treatment of seeds (for example cereals, cotton, beet, rape, grain fodder and vegetable seeds), for example in the form of coating or film formation. A form of application may be found in U.S. Pat. No. 3,989,501, col. 7, 1 17–23. Likewise in FR-A-2,588,442. Flowables may also be used.

In general, these formulations are already known; see, e.g., "Catalogue of pesticide formulation types and international coding system", published by GIFAP technical monograph no. 2, pages 12 to 14, revised January 1984.

Apart from the applications already described above, the products according to the invention exhibit, in addition, excellent biocidal activity with respect to many other varieties of microorganisms, among which there may be mentioned, without implied limitation, fungi such as those of the genera:

Pullularia, such as the species *P. pullulans,*
Chaetomium, such as the species *C. globosum,*
Aspergillus, such as the species *Aspergillus niger,*
Coniophora such as the species *C. puteana.*

By reason of their biocidal activity, the products of the invention permit effective control of microorganisms whose proliferation creates many problems in agricultural and industrial fields. To this end, they are most especially well suited to the protection of plants or industrial products such as wood, leather, paint, paper, rope, plastics and industrial water circuits.

They are most especially suitable for the protection of lignocellulose products, and in particular of wood, both wood used in furniture and constructional timber and wood exposed to the weather such as fence posts, vine stakes and railway sleepers.

The compounds according to the invention, used alone or in the form of compositions as defined above in the treatment of wood, are generally employed with organic solvents, and can be optionally combined with one or more known biocidal products such as pentachlorophenol, metal salts, in particular of copper, manganese, cobalt, chromium or zinc derived from inorganic or carboxylic acids (heptanoic, octanoic and naphthenic acids); organic tin complexes, mercaptobenzothiazole, and insecticides such as pyrethroids or organochlorine compounds.

They exhibit, finally, excellent selectivity with respect to crops.

They are advantageously applied at doses of 0.005 to 5 kg/ha, and more especially 0.01 to 1 kg/ha.

For their use in practice, the compounds according to the invention are rarely used alone. More often than not, they form part of compositions. These compositions which are useable for the protection of plants against fungal diseases or in compositions for regulating plant growth, contain as active substance a compound according to the invention, as described above, in combination with solid or liquid vehicles which are acceptable in agriculture and/or surfactant agents which are also acceptable in agriculture. The usual inert vehicles and the usual surfactant agents are useable, in particular.

These compositions customarily contain between 0.5 and 95% of compound according to the invention.

The term "vehicle" in the present description denotes a natural or synthetic organic or inorganic substance with which the active substance is combined in order to facilitate its application on the plant, the seeds or the soil. This vehicle is hence generally inert and it must be acceptable in agriculture, in particular on the plant treated. The vehicle can be solid (clays, natural or synthetic silicates, silica, resins, waxes, solid fertilizers, and the like) or liquid (water, alcohols, ketones, petroleum cuts, aromatic or paraffinic hydrocarbons, chlorinated hydrocarbons, liquified gases, and the like).

The surfactant agent can be an emulsifying, dispersant or wetting agent of the ionic or nonionic type. There may be mentioned, e.g., polyacrylic acid salts, lignosulphonic acid salts, phenolsulphonic or naphthalenesulphonic acid salts, polycondensates of ethylene oxide with fatty alcohols or with fatty acids or with fatty amines, substituted phenols, (in particular alkylphenols or arylphenols), salts of sulphosuccinic acid esters, taurine derivatives (in particular alkyl taurides), and polycondensates of ethylene oxide with phosphoric acid esters of alcohols or phenols. The presence of at least one surfactant agent is generally essential when the active substance and/or the inert vehicle are not water-soluble and the carrier agent for the application is water.

For their application, the compounds of formula (I) are generally in the form of compositions; these compositions according to the invention are themselves in quite diverse solid or liquid forms.

As solid forms of compositions, there may be mentioned powders for dusting or dispersion (having a content of the compound of formula (I) which can range up to 100%) and granules, in particular those obtained by extrusion, by compaction, by impregnation of a granulated vehicle or by granulation from a powder (the content of the compound of formula (I) in these granules being between 1 and 80% for these latter cases).

As liquid forms of compositions, or forms designed to constitute liquid compositions when they are applied, there may be mentioned solutions, especially water-soluble concentrates, emulsifiable concentrates, emulsions, flowables, aerosols, wettable powders (or powder for spraying) and pastes.

The emulsifiable or soluble concentrates most often comprise 10 to 80% of active substance, the ready-for-application emulsions or solutions, for their part, containing 0.01 to 20% of active substance.

These compositions can also contain any other sort of ingredient such as, e.g. protective colloids, adhesives, thickeners, fixotropic agents, penetrating agents, stabilizers, sequestering agents, and the like, as well as other known active substances having pesticidal (and in particular insecticidal or fungicidal) properties or having plant growth-promoting properties (in particular fertilizers) or having plant growth-regulating properties. More generally, the compounds according to the invention may be combined with al l solid or liquid additives corresponding to the customary techniques for preparing formulations.

For example, in addition to the solvent, the emulsifiable concentrates can contain, when necessary, 2 to 20% of suitable additives such as the stabilizers, surfactant agents, penetrating agents, corrosion inhibitors, colourings or adhesives mentioned above.

The doses for use, in the case of a use of the compounds according to the invention as fungicides, can vary within wide limits, in particular according to the virulence of the fungi and the climatic conditions.

Generally speaking, compositions containing 0.5 to 5000 ppm of active substance are very suitable; these values are indicated for the ready-for-application compositions. ppm means "parts per million". The range from 0.5 to 5000 ppm corresponds to a range of $5 \times 10^{-5}$ to 0.5% (percentages by weight).

As regards the compositions suited to storage and transport, they contain, more advantageously, from 0.5 to 95% (by weight) of active substance.

Thus, the compositions for agricultural use according to the invention can hence contain the active substances according to the invention within very wide limits, ranging from $5 \times 10^{-5}$% to 95% (by weight).

By way of example, there follows the composition of a few concentrates:

| Example F (formulation) 1 | |
|---|---|
| Active substance | 400 g/l |
| Alkali metal dodecylbenzenesulphonate | 24 g/l |
| Condensate of nonylphenol with 10 molecules of ethylene oxide | 16 g/l |
| Cyclohexanone | 200 g/l |
| Aromatic solvent q.s. | 1 liter |

According to another formula for an emulsifiable concentrate, the following are used:

| Example F 2: | |
|---|---|
| Active substance | 250 g |
| Epoxidized vegetable oil | 25 g |
| Mixture of alkylarylsulphonate and ether of polyglycol and fatty alcohols | 100 g |
| Dimethylformamide | 50 g |
| Xylene | 575 g |

From these concentrates, emulsions of any desired concentration, which are especially suitable for application on leaves, may be obtained by dilution with water.

The flowables, also applicable by spraying, are prepared in such a way as to obtain a stable fluid product which does not settle out and they usually contain from 10 to 75% of active substance, from 0.5 to 15% of surfactant agents, from 0.1 to 10% of thixotropic agents, from 0 to 10% of suitable additives, such as antifoams, corrosion inhibitors, stabilizers, penetrating agents and adhesives and, as a vehicle, water or an organic liquid in which the active substance is sparingly soluble or insoluble: some organic solid substances or inorganic salts can be dissolved in the vehicle in order to assist in preventing sedimentation or as antifreeze for the water.

The wettable powders (or powder for spraying) are usually prepared in such a way that they contain 20 to 95% of active substance, and they usually contain, in addition to the solid vehicle, from 0 to 5% of a wetting agent, from 3 to 10% of a dispersant agent and, when necessary, from 0 to 10% of one or more stabilizers and/or other additives, such as penetrating agents, adhesives, or anti-caking agents, colourings, and the like.

By way of Example, there follow various compositions of wettable powders:

| Example F 3: | |
|---|---|
| Active substance | 50% |
| Calcium lignosulphonate (deflocculant) | 5% |
| Isopropylnaphthalenesulphonate (anionic wetting agent) | 1% |
| Anti-caking silica | 5% |
| Kaolin (filler) | 39% |

Another composition of a 70% strength powder for spraying uses the following constituents:

| Example F 4: | |
|---|---|
| Active substance | 700 g |
| Sodium dibutylnaphthalenesulphonate | 50 g |
| Condensation product in proportions 3:2:1 of naphthalenesulphonic acid, phenolsulphonic acid and formaldehyde | 30 g |
| Kaolin | 100 g |
| Whiting | 120 g |

Another composition of a 40% strength powder for spraying uses the following constituents:

| Example F 5: | |
|---|---|
| Active substance | 400 g |
| Sodium lignosulphonate | 50 g |
| Sodium dibutylnaphthalenesulphonate | 10 g |
| Silica | 540 g |

Another composition of a 25% strength powder for spraying uses the following constituents:

| Example F 6: | |
|---|---|
| Active substance | 250 g |
| Calcium lignosulphonate | 45 g |
| Mixture of equal parts by weight of whiting and hydroxyethyl cellulose | 19 g |
| Sodium dibutylnaphthalenesulphonate | 15 g |
| Silica | 195 g |
| Whiting | 195 g |
| Kaolin | 281 g |

Another composition of a 25% strength powder for spraying uses the following constituents:

| Example F 7: | |
|---|---|
| Active substance | 250 g |
| Isooctylphenoxy-polyoxyethylene-ethanol | 25 g |
| Mixture of equal parts by weight of whiting and hydroxyethylcellulose | 17 g |
| Sodium aluminosilicate | 543 g |
| Kieselguhr | 165 g |

Another composition of a 10% strength powder for spraying uses the following constituents:

| Example F 8: | |
|---|---|
| Active substance | 100 g |
| Mixture of sodium salts of sulphates of saturated fatty acids | 30 g |
| Condensation product of naphthalenesulphonic acid and formaldehyde | 50 g |
| Kaolin | 820 g |

To obtain these powders for spraying or wettable powders, the active substances are mixed intimately in suitable blenders with the additional substances and the mixtures are ground with mills or other suitable grinders. Powders for spraying are thereby obtained, whose wettability and suspendibility are advantageous; they may be suspended in water at any desired concentration and these suspensions are very advantageously useable, especially for application on the leaves of plants.

In place of wettable powders, pastes can be made. The conditions and procedures for making and using these pastes are similar to those for the wettable powders or powders for spraying.

As already stated, the aqueous emulsions and dispersions, for example the compositions obtained by diluting with water a wettable powder or an emulsifiable concentrate according to the invention, are included within the general scope of the present invention. The emulsions can be of the water-in-oil or oil-in-water type, and they can have a thick consistency like that of a "mayonnaise".

The granules designed to be laid on the soil are usually prepared in such a way that they are between 0.1 and 2 mm in size, and they can be manufactured by agglomeration or impregnation. In general, the granules contain 0.5 to 25% of active substance and 0 to 10% of additives such as stabilizers, slow-release modifying agents, binders and solvents.

According to an example of a granule composition, the following constituents are used:

| Example F 9: | |
|---|---|
| Active substance | 50 g |
| Epichlorohydrin | 2.5 g |
| Cetyl polyglycol ether | 2.5 g |
| Polyethylene glycol | 35 g |
| Kaolin (particle size: 0.3 to 0.8 mm) | 910 g |

In this particular case, the active substance is mixed with epichlorohydrin and the mixture is dissolved with 60 g of acetone. The polyethylene glycol and cetyl polyglycol ether are then added. The kaolin is wetted with the solution obtained and the acetone is then evaporated off under vacuum. A microgranule of this kind is advantageously used for controlling soil fungi.

The compounds of the formula (I) can also be used in the form of dusting powders; a composition comprising 50 g of active substance and 950 g of talc can also be used; a composition comprising 20 g of active substance, 10 g of finely divided silica and 970 g of talc can also be used; these constituents are mixed and ground and the mixture is applied by dusting.

The examples below, described without implied limitation, illustrate the preparation of the compounds according to the invention, as well as their use for controlling phytopathogenic fungi. The structures of the compounds described in these examples were confirmed by nuclear magnetic resonance (NMR) spectrometry and/or by infrared spectrometry.

EXAMPLE 1

Stage 1: Preparation of 2-(3-pyridyl)-2-ethyl-3-bromopropanenitrile

A three-necked round-bottomed flask equipped with a stirrer, a thermometer, a condenser and a dropping funnel is used.

The flask is charged successively with 2-(3-pyridyl)-butanenitrile (14.6 g), methylene bromide (30 cc) and methyltri(C8–C10 alkyl)ammonium chloride (Adogen 464) (3 g), and the mixture is kept stirred.

Sodium hydroxide (12 g) dissolved in water (12 cc) is then added.

The mixture is brought to 90° C. for 3 h. After it is cooled, water (20 cc) is added to the brownish solution, which is extracted with methylene chloride.

The combined organic phases are washed with water, dried over magnesium sulphate and then concentrated.

The crude oil obtained is chromatographed on a silica column (eluant: diisopropyl ether).

2-(3-Pyridyl)-2-ethyl-3-bromopropanenitrile (19.6 g) is obtained in the form of a pale yellow viscous oil. Yield 82%.

The characteristics of the intermediate compounds of formula XI, obtained in the same manner, are given below.

| Rc | Appearance | Yld |
|---|---|---|
| Et | Viscous oil | 82 |
| allyl | Viscous oil | 73 |
| i-Pr | Viscous oil | 67 |
| n-Pr | Viscous oil | 61 |
| $CH_2SiMe_3$ | m.p. 93.9° C. | 70 |
| n-Bu | Viscous oil | 71 |

Stage 2: Preparation of
2-(3-pyridyl)-2-ethyl-3-(4-chlorophenoxy)propanenitrile

The apparatus described in the above example is used. Dimethylformamide (100 ml) is introduced into the flask, followed by sodium hydride (3.75 g; 0.126 g-at.) (at a concentration of 80% in oil). 4-Chlorophenol (15.4 g; 0.12 mole), diluted in dimethylformamide (30 cc), is poured into the suspension, cooled to 10° C. The mixture is kept for 30 min at room temperature.

2-(3-Pyridyl)-2-ethyl-3-bromopropanenitrile (23.9 g; 0.1 mole), diluted in dimethylformamide (20 cc), is then added. The solution is brought to 100° C. for 6 hours. After it is cooled to 10° C., ice-cold water (300 cc) is added to the solution, and the mixture is then extracted with ethyl acetate (3×60 cc). The combined organic phases are washed successively with 10% strength aqueous $KHCO_3$ solution (100 cc) and then water (200 cc), and dried over magnesium sulphate and then concentrated.

The pasty residue obtained is chromatographed on a silica column (eluent: diisopropyl ether). A beige solid is obtained, which is recrystallized in a 50:50 diisopropyl ether/heptane mixture (40 cc) and yields 2-(3-pyridyl-2-ethyl-3-(4-chlorophenoxy)propanenitrile (18.6 g; 0.065 mole) in the form of a white solid, m.p. 82.1° C.

Yield (calculated with respect to 2-(3-pyridyl)-2-ethyl-3-bromopropanenitrile): 65%.

The compounds of Examples 2 to 25, which are collated in the attached table, and the nomenclature of which is stated after the examples, were obtained in the same manner.

TABLE I

Compounds corresponding to the general formula

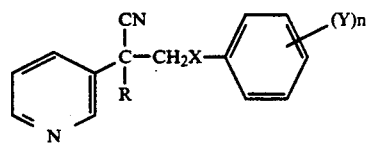

| Compound No. | R | X | Yn | Melting point °C. | Yield % |
|---|---|---|---|---|---|
| 1 | Et | O | p-Cl(Ph) | 82,1 | 65 |
| 2 | Et | S | p-Cl(Ph) | 51,3 | 79 |
| 3 | Et | S | p-F(Ph) | syrup | 51 |
| 4 | Et | S | p-Br(Ph) | 58 | 35 |
| 5 | Et | S | m,p-Cl2(Ph) | 79,9 | 52 |
| 6 | Et | O | p-Br(Ph) | 93,6 | 78 |
| 7 | Et | O | m,p-Cl2(Ph) | syrup | 69 |
| 8 | Et | O | o,p-Cl2(Ph) | 70,7 | −65 |
| 9 | Et | O | o,o,p-Cl3(Ph) | 37,1 | 48 |
| 10 | allyl | O | p-Cl(Ph) | 57,8 | 78 |
| 11 | allyl | O | o,p-Cl2(Ph) | syrup | 62 |
| 12 | allyl | O | p-Br(Ph) | 62,8 | 66 |
| 13 | i-Pr | O | p-Br(Ph) | 62,4 | 70 |
| 14 | allyl | O | m,p-Cl2(Ph) | syrup | 65 |
| 15 | i-Pr | O | m,p-Cl2(Ph) | syrup | 60 |
| 16 | Et | O | m,m-Cl2(Ph) | 94,2 | 72 |
| 17 | n-Pr | O | p-Cl(Ph) | 77,9 | 61 |
| 18 | n-Pr | O | m,p-Cl2(Ph) | syrup | 54 |
| 19 | Et | O | p-OCF3(Ph) | syrup | 75 |
| 20 | CH2—Si(Me)3 | O | p-Cl(Ph) | 76,9 | 32 |
| 21 | CH2—Si(Me)3 | O | m,p-Cl2(Ph) | 90,2 | 61 |
| 22 | Et | O | p-F(Ph) | 79,2 | 63 |
| 23 | Et | O | m-F(Ph) | 61,7 | 51 |
| 24 | Et | O | m,m,p-Cl3(Ph) | 116,1 | 50 |
| 25 | Et | O | o,p-Br2(Ph) | 101,2 | 51 |

Ph: phenylene ring
o: ortho-substituted
p: para-substituted
m: meta-substituted

EXAMPLE 26

Stage 1: Preparation of 2-(3-pyridyl)-4-(4-chlorophenoxy)butanenitrile

A three-necked round-bottomed flask equipped with a stirrer and provided with a thermometer, a condenser and a dropping funnel is used.

Anhydrous DMF (250 cc) is introduced into the flask, followed by sodium hydride (3.15 g; 0.105 mole) (at a concentration of 80% in oil).

(3-Pyridyl)acetonitrile (11.8 g; 0.1 mole), diluted in DMF (30 ml), is then added dropwise.

1-Bromo-2-(4-chlorophenoxy)ethane (23.5 g; 0.1 mole), diluted in DMF (30 cc), is then added dropwise to the salt formed.

The solution is kept stirred for 2 hours at 25° C. The mixture is then poured into ice-cold water (500 cc), and thereafter extracted with ethyl acetate (3×150 cc). The combined organic phases are washed with water (300 cc), dried over magnesium sulphate and then concentrated.

The crude oil obtained is taken up with ethyl ether (100 cc).

The white precipitate which appears rapidly is filtered on a sinter; mass collected 3.5 g, m.p. 141° C. This is the disubstituted derivative of formula (X).

The concentrated filtrate is chromatographed on a silica column. 2-(3-Pyridyl)-4-(4-chlorophenoxy)butanenitrile (16.8 g) is obtained in the form of a pale yellow oil. Yield: 62%.

Stage 2: Preparation of 2-(3-pyridyl)-2-methyl-4-(4-chlorophenoxy)butanenitrile The same apparatus as that described in stage 1 is used. Anhydrous DMF (100 cc) is introduced into the flask, followed by sodium hydride (1.57 g; 5.25×10⁻² g-at.).

2-(3-Pyridyl)-4-(4-chlorophenoxy)butanenitrile (13.6 g; 0.05 mole), diluted in DMF (20 cc), is then added dropwise. Methyl iodide (3.2 cc; 0.05 mole), diluted in DMF (20 cc), is then poured in.

The solution is kept stirred for 3 hours at 25° C.

The mixture is then poured into ice-cold water (300 cc), and thereafter extracted with ethyl acetate (3×60 cc). The combined organic phases are washed with water (150 cc), dried over magnesium sulphate and then concentrated.

The crude oil obtained is chromatographed on a silica column (eluant: diisopropyl ether), and yields 2-(3-pyridyl)-2-methyl-4-(4-chlorophenoxy)butanenitrile (7.7 g) in the form of a yellow oil. Yield: 54%.

TABLE II

Compounds corresponding to the general formula

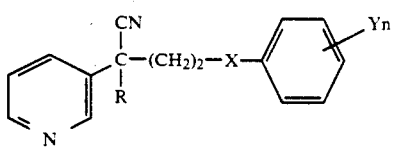

| Compound No. | R | X | | Appearance | Yield % |
|---|---|---|---|---|---|
| 26 | H | O | p-Cl(Ph) | oil | 62 |
| 27 | Me | O | p-Cl(Ph) | oil | 54 |
| 28 | Et | O | p-Cl(Ph) | oil | 31 |
| 29 | n-Pr | O | P-Cl(Ph) | pale yellow crystals m.p. 46.1° C. | 26 |
| 30 | allyl | O | p-Cl(Ph) | oil | 41 |
| 31 | Et | O | m,p-Cl₂(Ph) | oil | 44 |
| 32 | n-Pr | O | m,p-Cl₂(Ph) | oil | 52 |
| 33 | H | S | p-Cl(Ph) | oil | 40 |
| 34 | Me | S | p-Cl(Ph) | oil | 30 |
| 35 | Et | S | p-Cl(Ph) | oil | 66 |
| 36 | n-Pr | S | p-Cl(Ph) | oil | 37 |
| 37 | H | S | p-Br(Ph) | oil | 45 |
| 38 | Me | S | p-Br(Ph) | white crystals m.p. 68.8° C. | 54 |
| 39 | Et | S | p-Br(Ph) | oil | 81 |
| 40 | n-Pr | S | p-Br(Ph) | oil | 88 |

Ph: phenylene ring

Nomenclature

Example 2:
2-(3-Pyridyl)-2-ethyl-3-(4-chlorothiophenoxy)propanenitrile

Example 3:
2-(3-Pyridyl)-2-ethyl-3-(4-fluorothiophenoxy)propanenitrile

Example 4:
2-(3-Pyridyl)-2-ethyl-3-(4-bromothiophenoxy)propanenitrile

Example 5:
2-(3-Pyridyl)-2-ethyl-3-(3,4-dichlorothiophenoxy)propanenitrile

Example 6:
2-(3-Pyridyl)-2-ethyl-3-(4-bromophenoxy)propanenitrile

Example 7:
2-(3-Pyridyl)-2-ethyl-3-(3,4-dichlorophenoxy)propanenitrile

Example 8:
2-(3-Pyridyl)-2-ethyl-3-(2,4-dichlorophenoxy)propanenitrile

Example 9:
2-(3-Pyridyl)-2-ethyl-3-(2,4,6-trichlorophenoxy)propanenitrile

Example 10:
2-(3-Pyridyl)-2-allyl-3-(4-chlorophenoxy)propanenitrile

Example 11:
2-(3-Pyridyl)-2-allyl-3-(2,4-dichlorophenoxy)propanenitrile

Example 12:
2-(3-Pyridyl)-2-allyl-3-(4-bromophenoxy)propanenitrile

Example 13:
2-(3-Pyridyl)-2-methylethyl-3-(4-bromophenoxy)propanenitrile

Example 14:

2-(3-Pyridyl)-2-allyl-3-(3,4-dichlorophenoxy)-propanenitrile

Example 15:
2-(3-Pyridyl)-2-methylethyl-3-(3,4-chlorophenoxy)-propanenitrile

Example 16:
2-(3-Pyridyl)-2-ethyl-3-(3,5-dichlorophenoxy)-propanenitrile

Example 17:
2-(3-Pyridyl)-2-propyl-3-(4-chlorophenoxy)propanenitrile

Example 18:
2-(3-Pyridyl)-2-propyl-3-(3,4-dichlorophenoxy)-propanenitrile

Example 19:
2-(3-Pyridyl)-2-ethyl-3-(4-trifluoromethoxyphenoxy)-propanenitrile

Example 20:
2-(3-Pyridyl)-2-trimethylsilylmethyl-3-(4-chlorophenoxy)propanenitrile Example 21:
2-(3-Pyridyl)-2-trimethylsilylmethyl-3-(3,4-dichlorophenoxy)propanenitrile Example 22:
2-(3-Pyridyl)-2-ethyl-3-(4-fluorophenoxy)propanenitrile Example 23:
2-(3-Pyridyl)-2-ethyl-3-(3-fluorophenoxy)propanenitrile Example 24:
2-(3-Pyridyl)-2-ethyl-3-(3,4,5-trichlorophenoxy)-propanenitrile Example 25:
2-(3-Pyridyl)-2-ethyl-3-(2,4-dibromophenoxy)-propanenitrile Example 26:
2-(3-Pyridyl)-4-(4-chlorophenoxy)butanenitrile Example 27:
2-(3-Pyridyl)-2-methyl-4-(4-chlorophenoxy)butanenitrile Example 28:
2-(3-Pyridyl)-2-ethyl-4-(4-chlorophenoxy)butanenitrile Example 29:
2-(3-Pyridyl)-2-propyl-4-(4-chlorophenoxy)butanenitrile Example 30:
2-(3-Pyridyl)-2-allyl-4-(4-chlorophenoxy)butanenitrile Example 31:
2-(3-Pyridyl)-2-ethyl-4-(3,4-dichlorophenoxy)butanenitrile Example 32:
2-(3-Pyridyl)-2-propyl-4-(3,4-dichlorophenoxy)-butanenitrile Example 33:
2-(3-Pyridyl)-4-(4-chlorothiophenoxy)butanenitrile Example 34:
2-(3-Pyridyl)-2-methyl-4-(4-chlorothiophenoxy)-butanenitrile Example 35:
2-(3-Pyridyl)-2-ethyl-4-(4-chlorothiophenoxy)butanenitrile Example 36:
2-(3-Pyridyl)-2-propyl-4-(4-chlorothiophenoxy)-butanenitrile Example 37:
2-(3-Pyridyl)-4-(4-bromothiophenoxy)butanenitrile Example 38:
2-(3-Pyridyl)-2-methyl-4-(4-bromothiophenoxy)-butanenitrile Example 39:
2-(3-Pyridyl)-2-ethyl-4-(4-bromothiophenoxy)butanenitrile Example 40:
2-(3-Pyridyl)-2-propyl-4-(4-bromothiophenoxy)-butanenitrile Example - In vitro test on seed fungi and soil fungi The action of the compounds according to the invention is studied on the following fungi, responsible for diseases of cereals and other plants:

11) *Pyrenophorae avenae*
6) *Septoria nodorum*
12) *Helminthosporium teres*
9) *Fusarium roseum*
8) *Fusarium nivale*
7) *Fusarium culmorum*
13) *Rhizoctonia cerealis*
14) *Septoria tritici*
1) *Botrytis cinerea* sensitive to carbendazim and cyclic imides
2) *Botrytis cinerea* resistant to carbendazim and cyclic imides
5) *Pseudocercosporella herpotrichoides*
3) *Fusarium oxysporum F.sp melonis*
4) *Rhizoctonia solani*
10) *Helminthosporium gramineum*

The numbers appearing before the names will be used to denote these fungi in Table III.

For each test, the procedure is as follows: a nutrient medium consisting of potato, glucose and agar (PDA medium) is introduced in the super cooled state into a series of Petri dishes (20 cc per dish) after sterilization in an autoclave at 120° C.

During the filling of the dishes, an acetone solution of the active substance is injected into the medium in the super cooled state, to obtain the desired final concentration.

Petri dishes similar to the above, into which are poured similar amounts of a nutrient medium not containing any active substance, are taken as a control.

After 24 or 48 h, each dish is inoculated by depositing a fragment of mycelium originating from a previous culture of the same fungus.

The dishes are stored for 2 to 10 days (according to the fungus tested) at 22° C., and the growth of the fungus in the dishes containing the active substance under test is then compared with that of the same fungus in the dish used as a control.

The degree of inhibition of the fungus in question for a dose of 30 ppm is thereby determined for each test compound. The results are shown in the Table below.

TABLE III

|   | 1  | 2  | 3   | 4  | 5   | 6   | 7   | 8  | 9  | 10  | 11  | 12  | 13  | 14 |
|---|----|----|-----|----|-----|-----|-----|----|----|-----|-----|-----|-----|----|
| 1 | 95 | 95 | 100 | 50 | 100 | 100 | 95  | 95 | 90 | 100 | 100 | 100 | 95  |    |
| 2 | 95 | 95 | 95  | 0  | 90  | 90  | 100 | 80 | 80 | 95  | 95  | 95  | 80  |    |
| 3 | 95 | 95 | 90  | 0  | 95  | 90  | 95  | 80 | 80 | 90  | 90  | 90  | 80  |    |
| 4 | 95 | 95 | 80  | 0  | 95  | 95  | 100 | 95 | 80 | 90  | 90  | 90  | 80  |    |
| 5 | 95 | 95 | 80  | 0  | 95  | 95  | 95  | 90 | 50 | 90  | 90  | 90  | 80  |    |

TABLE III-continued

| | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 6 | 95 | 95 | 95 | 50 | 95 | 95 | 100 | 90 | 90 | 95 | 95 | 95 | 80 | |
| 7 | 95 | 95 | 95 | 50 | 100 | 95 | 95 | 90 | 80 | 90 | 90 | 95 | 90 | |
| 8 | 90 | 95 | 95 | 50 | 100 | 95 | 95 | 80 | 80 | 95 | 95 | 95 | 90 | 80 |
| 9 | 80 | 80 | 0 | 0 | 0 | 0 | 90 | 80 | 80 | 80 | 80 | 80 | 80 | 100 |
| 10 | 95 | 95 | 95 | 50 | 100 | 100 | 100 | 100 | 95 | 95 | 95 | 100 | 90 | |
| 11 | 80 | 80 | 80 | 0 | 90 | 80 | 100 | 95 | 90 | 90 | 95 | 100 | 80 | |
| 12 | 90 | 90 | 90 | 80 | 95 | 90 | 95 | 95 | 90 | 95 | 95 | 95 | 95 | 50 |
| 13 | 95 | 95 | 95 | 90 | 100 | 95 | 95 | 95 | 90 | 95 | 100 | 95 | 90 | |
| 14 | 80 | 90 | 80 | 50 | 90 | 90 | 95 | 90 | 90 | 95 | 95 | 95 | 95 | 50 |
| 15 | 80 | 90 | 0 | 80 | 90 | 90 | 100 | 95 | 95 | 90 | 90 | 90 | 90 | |
| 16 | 80 | 80 | 0 | 0 | 0 | 0 | 90 | 90 | 50 | 0 | 90 | 80 | 0 | |
| 17 | 90 | 90 | 80 | 80 | 80 | 80 | 95 | 95 | 90 | 95 | 95 | 100 | 95 | |
| 18 | 90 | 90 | 0 | 0 | 0 | 0 | 95 | 90 | 80 | 90 | 90 | 90 | 90 | |
| 19 | 95 | 95 | 95 | 0 | 100 | 90 | 100 | 80 | 80 | 95 | 90 | 90 | 80 | 100 |
| 20 | 50 | 50 | 0 | 0 | 0 | 0 | 80 | 80 | 80 | 80 | 80 | 80 | 80 | |
| 21 | 0 | 0 | 0 | 0 | 0 | 0 | 80 | 80 | 80 | 80 | 80 | 80 | 80 | |
| 22 | 100 | 100 | 100 | 0 | 100 | 100 | 100 | 80 | 80 | 90 | 100 | 100 | 80 | 80 |
| 23 | 100 | 100 | 90 | 0 | 90 | 100 | 95 | 80 | 50 | 90 | 95 | 95 | 50 | 100 |
| 24 | 50 | 50 | 50 | 0 | 90 | 90 | 80 | 80 | 50 | 90 | 80 | 80 | 0 | 50 |
| 25 | 50 | 80 | 80 | 80 | 90 | 80 | 95 | 80 | 80 | 100 | 95 | 95 | 80 | |
| 26 | 0 | 0 | 50 | 80 | 80 | 80 | 90 | 80 | 80 | 90 | 90 | 90 | 90 | 100 |
| 27 | 90 | 90 | 90 | 80 | 100 | 100 | 95 | 90 | 80 | 90 | 90 | 90 | 80 | 50 |
| 28 | 95 | 95 | 90 | 80 | 95 | 95 | 80 | 80 | 80 | 95 | 95 | 95 | 95 | |
| 29 | 90 | 90 | 90 | 80 | 100 | 90 | 100 | 95 | 90 | 95 | 95 | 95 | 95 | |
| 30 | 95 | 95 | 90 | 90 | 100 | 100 | 100 | 90 | 90 | 95 | 100 | 100 | 90 | 80 |
| 31 | 90 | 95 | 80 | 80 | 95 | 100 | 90 | 90 | 50 | 95 | 90 | 90 | 80 | |
| 32 | 80 | 80 | 80 | 50 | 90 | 90 | 95 | 90 | 80 | 90 | 95 | 95 | 80 | |
| 33 | 80 | 80 | 80 | 80 | 90 | 50 | 90 | 50 | 50 | 80 | 80 | 80 | 50 | |
| 34 | 80 | 80 | 80 | 80 | 90 | 90 | 90 | 50 | 50 | 90 | 95 | 95 | 80 | 50 |
| 35 | 80 | 80 | 80 | 0 | 90 | 90 | 90 | 50 | 50 | 90 | 90 | 90 | 80 | |
| 36 | 50 | 50 | 50 | 80 | 80 | 80 | 90 | 50 | 50 | 90 | 95 | 95 | 80 | |
| 37 | 80 | 90 | 50 | 80 | 90 | 90 | 90 | 50 | 50 | 80 | 90 | 90 | 80 | 100 |
| 38 | 80 | 90 | 50 | 0 | 95 | 95 | 90 | 50 | 50 | 90 | 90 | 90 | 80 | 100 |
| 39 | 0 | 80 | 80 | 0 | 90 | 90 | 90 | 80 | 80 | 80 | 90 | 95 | 80 | |
| 40 | 0 | 80 | 80 | 0 | 90 | 90 | 90 | 80 | 80 | 80 | 90 | 95 | 80 | |

Example: In vivo test on *Botrytis cinerea* of tomatoes

An aqueous suspension of the active substance under test having the following composition is prepared by fine grinding:

| | |
|---|---|
| Active substance under test | 40 mg |
| Tween 80 (surfactant agent consisting of a monolaurate of a polycondensate with ethylene oxide derived from sorbitan) | 0.4 cc |
| Water | 40 cc |

This aqueous suspension is then diluted with water to obtain the desired concentration.

Tomatoes (Marmande variety) cultivated in a greenhouse, from 60 to 75 days old, are treated by spraying with aqueous suspensions of the composition described, at a concentration of active substance of 1 g/l (1000 ppm). The test is repeated twice with each concentration.

After 24 hours, the leaves are cut off and placed in 2 Petri dishes (diameter 11 cm), the bottom of which has been lined beforehand with a disc of wet filter paper (5 leaflets per dish).

The inoculum is then introduced using a syringe, by depositing drops (3 drops per leaflet) of a spore suspension. This suspension of *Botrytis cinerea* spores was obtained from a 15-day culture, subsequently suspended in a nutrient solution (80,000 units/cc). The effect is checked approximately 4 to 6 days after contamination, by comparison with an untreated control. The percentage protection relative to the untreated control is thereby assessed.

Under these conditions, it is observed that, at a concentration of 1,000 mg/l, the percentage protection was, respectively, at least 75% for the following compounds, 1, 4, 5, 6, 7, 10, 12, 13, 15, 17, 18, 22, 23, 27, 28, 29, 30 and 35.

In vivo test on barley mildew in preventive treatment

An aqueous suspension of the active substance under test having the following composition is prepared by fine grinding:

| | |
|---|---|
| Active substance under test | 60 mg |
| Tween 80 (surfactant agent consisting of a monolaurate of a polycondensate with ethylene oxide derived from sorbitan) diluted to 1/10 | 0.3 cc |
| Water | 60 cc |

This aqueous suspension is then diluted with water to obtain the desired concentration.

Barley seedlings (*Hordeum vulgare*), Berac variety, are cultivated in pots. Five to six days after sowing, their foliage is treated by spraying a suspension (8 cc) of the active substance in distilled water containing Tween 80, at the desired concentration, on each seedling.

Each concentration of the active substance is subjected to three repetitions. The control plants are treated in the same manner but without active substance.

On the day following the treatment, after being dried, the plants are contaminated by dusting with spores of barley mildew (*Erysiphe graminis*), and then kept in a greenhouse at 22° C. plus or minus 2° C., at 60 to 80% relative humidity.

Fourteen days after treatment with the suspension of the active substance, the percentage inhibition of the growth of the fungus, by comparison with the untreated control, is assessed.

Under these conditions, it is observed that, at a concentration of 1,000 mg/l, the percentage inhibition of the growth of the fungus was, respectively:

at least 75% for the compounds: 5, 7, 9, 18, 20, 22 and 23.

Example- In vivo test on "*Puccina recondita*" responsible for wheat rust

Wheat, sown in pots in loam, is treated at the 10-cm height stage by spraying with aqueous emulsions (referred to as slurries) of the same composition as that described in the previous example and at various concentrations of the test compound. The test is repeated twice with each concentration.

After 24 hours, an aqueous suspension of spores (50,000 sp/cc) is sprayed onto the wheat; this suspension was obtained from contaminated plants. The wheat is then placed for 48 hours in an incubation cell at approximately 18° C. and at 100% relative humidity.

At the end of these 2 days, the relative humidity is brought back to 60%. The check on the state of the plants is carried out between the 11th and the 15th day after contamination, by comparison with the untreated control.

At a dose of 1 g/l, protection of at least 75% was obtained with the compounds 1, 4, 6, 7, 10, 13, 19, 20, 28 and 29.

Example- In vivo test on "*Piricularia oryzae*" responsible for piriculariosis of rice (rice blast)

Rice, sown in pots in a 50:50 mixture of enriched peat and pozzolana, is treated at the 10-cm height stage by spraying with an aqueous emulsion (referred to as a slurry) defined above having the concentration stated below. The experiment is twice repeated. After 24 hours, the plants are treated, by application on the leaves, with a suspension of spores obtained in a pure culture.

The plants thus treated and contaminated are then incubated at 25°-28° C. in saturating humidity for 24 hours, and then in a moist chamber in a greenhouse at 25°-28° C.

The reading is carried out 8 days after contamination. Under these conditions, the following results are observed: at a dose of 1 g/l, protection of at least 75% is obtained with the compounds 1, 2, 4, 6, 7, 8, 9, 10, 11, 12, 13, 14, 15, 16, 20, 22, 23, 24, 29, 30, 32, 37 and 38.

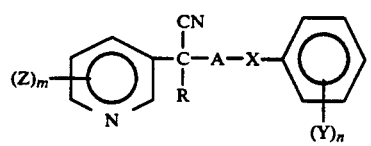
(I)

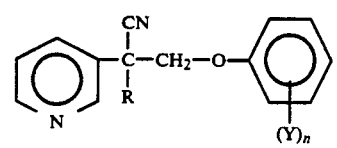
(II)

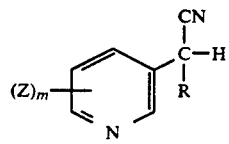
(III)

(Hal)$_2$CH$_2$ (IV)

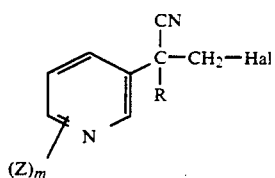
(V)

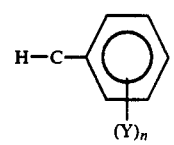
(VI)

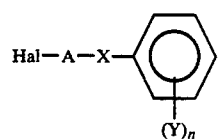
(VII)

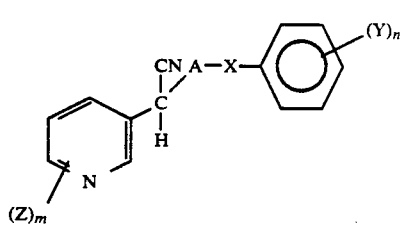
(VIII)

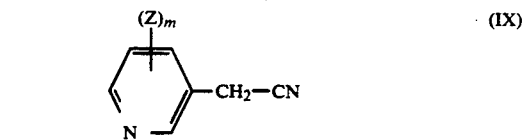
(IX)

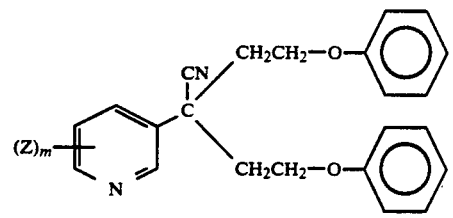
(X)

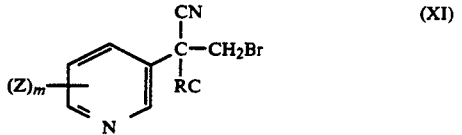
(XI)

We claim:

1. A compound of the formula

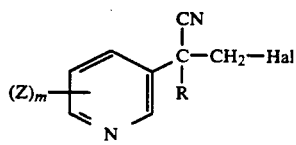
(V)

wherein:
Hal denotes a halogen atom;
R denotes:
a lower alkyl radical, optionally substituted with one or more substituents selected from the group consisting of halogen atoms, lower alkoxy radicals, lower alkylthio radicals and a radical $(CH_2)_xSiR_1R_2R_3$, wherein x is 0 or 1 and $R_1$, $R_2$ and $R_3$, which may be identical or different, are lower alkyl, lower alkoxy, aryl or aralkyl;

a 3- to 7-membered cycloalkyl radical selected from the group consisting of cyclopropyl, cyclobutyl, cyclopentyl and cyclohexyl, which is optionally substituted in the same manner as the lower alkyl radical;

an aralkyl radical optionally substituted in the same manner as the lower alkyl radical; or a mono- or polyunsaturated lower alkenyl or alkynyl radical, optionally substituted in the same manner as the lower alkyl radical, with the proviso that there is no unsaturation at the alpha-position with respect to the carbon bearing the CN group;

Z denotes a lower alkyl or lower alkoxy radical; and m denotes 0, 1 or 2, the groups Z being identical or different when m is 2.

2. The compound of formula (V) as claimed in claim 1, wherein R denotes:

a lower alkyl radical, optionally substituted with one or more substituents selected from the group consisting of halogen atoms, a lower alkoxy radical and a radical $-(CH_2)_xSiR_1R_2R_3$, wherein x is 0 or 1 and $R_1$, $R_2$ and $R_3$, which may be identical or different, are lower alkyl, lower alkoxy or aryl; or an alkenyl radical, optionally substituted as when R denotes alkyl; and m denotes 0.

3. The compound of formula (V) as claimed in claim 1, wherein R is a $C_1$-$C_6$ alkyl radical.

4. A compound according to claim 1, wherein Hal is a bromine atom and m is zero.

5. The compound according to claim 2, wherein R is ethyl.

6. The compound according to claim 2, wherein R is allyl.

7. The compound according to claim 2, wherein R is isopropyl.

8. The compound according to claim 2, wherein R is n-propyl.

9. The compound according to claim 2, wherein R is $-CH_2Si(CH_3)_3$.

10. The compound according to claim 2, wherein R is n-butyl.

* * * * *